United States Patent [19]

Stern et al.

[11] Patent Number: 4,681,577
[45] Date of Patent: Jul. 21, 1987

[54] DISPOSABLE URINARY AND FECAL WASTE CONTAINMENT PRODUCT

[75] Inventors: Beth A. Stern, Yardley, Pa.; Dennis C. Holtman, Flemington, N.J.

[73] Assignee: Personal Products Company, Milltown, N.J.

[21] Appl. No.: 746,612

[22] Filed: Jun. 19, 1985

Related U.S. Application Data

[63] Continuation-in-part of Ser. No. 535,192, Sep. 23, 1983, abandoned.

[51] Int. Cl.⁴ .............................................. A61F 13/16
[52] U.S. Cl. .................................... 604/378; 604/368; 604/385 R; 604/370; 604/389; 604/390; 604/379; 604/380
[58] Field of Search ............... 604/348, 347, 385, 369, 604/387, 368, 378, 397, 393, 370, 379, 380

[56] References Cited

U.S. PATENT DOCUMENTS

| | | | |
|---|---|---|---|
| 2,069,092 | 1/1937 | Jackson | 604/397 |
| 3,525,337 | 8/1970 | Simons et al. | 604/374 |
| 3,805,790 | 4/1974 | Kaczmarzyk et al. | 604/387 |
| 4,372,312 | 2/1983 | Fendler | 604/370 |

*Primary Examiner*—C. Fred Rosenbaum
*Assistant Examiner*—Sherri E. Vinyard
*Attorney, Agent, or Firm*—Nancy A. Bird

[57] ABSTRACT

The invention provides a disposable urinary and fecal waste containment product suitable for active adults. The product has a high liquid impact capacity, high liquid retention, contains fecal waste without leakage and allows the skin of the wearer to remain dry. The product has a liquid-impermeable substantially flexible shell containing a superstructure associated with an absorbent medium and a rear portion with a superstructure of three-dimensional characteristics with sufficient friction to prevent movement of fecal matter laterally.

19 Claims, 12 Drawing Figures

DISPOSABLE URINARY AND FECAL WASTE CONTAINMENT PRODUCT

This is a continuation-in-part of copending application Ser. No. 535,192, filed Sept. 23, 1983 now abandoned.

BACKGROUND OF THE INVENTION

The present invention relates to an entirely new concept of providing a disposable urinary and fecal waste containment product. The product is particularly suitable for active adults and contains adult discharges of urine and fecal waste. The product has a high liquid impact capacity, high liquid retention, contains fecal waste without leakage and allows the skin of the wearer to remain dry.

Disposable absorbent products have been known for some time, incuding such products as disposable diapers, sanitary napkins, wound dressings, bandages, incontinent pads, adult diaper and urinary containment products, and the like. These products incorporate an absorbent batt which is used to absorb and hold or contain body fluids. Initially, in many of these products, especially diapers and sanitary napkins, the absorbent batt comprised what is termed "wadding" or plies of tissue. The wadding was disposed between a liquid-impermeable backing and a liquid-permeable facing and the plies of tissue were used to absorb and, hopefully, contain the liquid within the product. A diaper which utilizes such an absorbent batt is disclosed in U.S. Pat. No. Re. 26,151.

The wadding type of product was replaced, for the most part, by an improved absorbent batt which comprises what is termed "fluffed woodpulp fibers". This absorbent batt comprises a layer of individualized woodpulp fibers with the layer having substantial thickness. A diaper which incorporates such a fluffed woodpulp absorbent batt is described in U.S. Pat. No. 2,788,003. This diaper had improved absorbent capacity and somewhat better containment than a diaper using a wadding layer. Also, the fluffed woodpulp layer is quite soft, flexible, and conformable, and, hence, produces an improved diaper over diapers using wadding as the absorbent layer.

Though the fluffed woodpulp absorbent batts have improved capacity, the efficiency with which the capacity is used in a diaper or sanitary napkin is poor. The reason for this is that the fluid to be absorbed is generally deposited in a localized area within the absorbent batt, and the ability of the fluid to move along the plane of the batt is poor. The fluid tends to follow a radial wicking path and consequently moves to the closest edge of the batt where it generally is no longer contained and the product leaks.

U.S. Pat. No. 3,017,304 discloses an absorbent product which incorporates in the product a densified paperlike layer. This paper-like layer acts as a wick, i.e., liquid which is placed on the layer tends to move rapidly along the plane of the layer. When incorporated in combination with fluffed woodpulp fiber, the resultant product uses the absorbent capacity of the fluffed woodpulp much more efficiently. Diapers which incorporate this paper-like layer combined with fluffed woodpulp are disclosed and described in U.S. Pat. Nos. 3,612,055 and 3,938,522. This concept of combining wicking ability, or a capillary skin or layer, with fluffed woodpulp fibers has gained wide acceptance in many absorbent products including disposable diapers and sanitary napkins. Even though these products make much greater use of the capacity of the absorbent batt, they still do not totally contain the absorbed liquid. It is probable that these products will leak before the full capacity of the batt is used for the absorption or, at the very least, before the entire liquid void by the user is absorbed. This is especially true when pressure is placed on the batt while wet. For example, a baby sitting down on a previously wetted diaper will very often cause the batt to leak.

An incontinent adult faces not only the problems of the infant but many other problems. First, the void of an adult generally is much higher in volume than that of an infant. Second, a bulge under clothing is accepted by society for an infant, but the ambulatory adult with an incontenance problem longs for a product which is not visible through ordinary clothing. Third, the proportions and shape of the legs and torso of the adult differs considerably from those of an infant. Therefore, a mere enlargement of an infant diaper, such as that shown in U.S. Pat. No. 4,253,461 is not a satisfactory product.

In the adult incontinent product marketplace, a product is needed which has a large storage capacity and which will also retain fecal waste matter. Such containers have been suggested, however these containers have been substantially rigid, have a tendency to dislodge and not be in the proper position and are quite uncomfortable. A product with a substantially large capacity with an ability to move liquid away from the void zone which is disposable, which is comfortable and which does not substantially show through wearing apparel is needed in the marketplace.

A number of years ago, "superabsorbent materials", i.e., materials which will absorb many times their weight of liquid, were developed. Since the development of such materials, attempts to incorporate them in absorbent products such as diapers to enhance the absorption performance of these products have been made. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water-insoluble cross-linked hydrocolloid polymer as the superabsorbent material.

Even though superabsorbent materials have been available for some time, they have not gained wide acceptance in absorbent products such as disposable diapers, and sanitary napkins. A primary reason for this lack of acceptance of superabsorbents is failure to develop a product capable of economically utilizing the highly increased absorptive capacity of the superabsorbent material. In order to economically utilize a superabsorbent, the liquid being absorbed must be readily accepted and placed in contact with the superabsorbent material. Furthermore, as the superabsorbent material absorbs liquid, it must be allowed to swell. If the superabsorbent is prevented from swelling, it will cease absorbing liquid. Hence, if the superabsorbent material is to function in absorbent products, such as diapers and sanitary napkins, wherein the liquid to be absorbed is placed in a small void area, the structure of the absorbent layer containing superabsorbent materials must have certain characteristics. Over the years, a number of techniques have been disclosed in an attempt to provide structures which make efficient use of the superabsorbent material. Such products are disclosed in U.S. Pat. Nos. 4,103,062; 4,102,340; and 4,235,237. In addition, methods for incorporating superabsorbents into suitable layers of suitable configurations which can be placed in an absorbent product, are disclosed in U.S. Pat. Nos. 4,186,165; 4,340,057; and 4,364,992. To date, none of these products has met with any substantial commercial success.

The present invention provides an entirely new disposable urinary and fecal waste containment product which possesses a large storage capacity which is soft and comfortable, which can be designed so as not to be particularly apparent through normal clothing and which utilizes a substantial portion of the absorptive capacity of superabsorbent materials. In addition, the new absorbent product will contain absorbed liquid and deposited fecal waste matter even when pressure is placed upon the product during use.

SUMMARY OF THE INVENTION

The present invention provides a disposable urinary and fecal waste containment product. This product comprises a liquid-impermeable substantially flexible shell having a depth of at least about 0.25" and having a front urinary portion and a rear fecal portion. The front portion generally is narrower and has an area less than 70% of the area of the rear portion. The front portion has a first superstructure placed in and substantially filling the front portion of the shell. It also has an absorbent medium which is in intimate contact with at least a portion of the superstructure. The superstructure is at least slightly compressible and capable of maintaining a void volume of liquid. The superstructure is comprised of hydrophobic, wet resilient, dry resilient fibers, fibrous web, foam or mixtures thereof. The rear portion has a second superstructure which also is placed in and substantially fills the rear portion of the shell. This superstructure is at least slightly compressible and has three-dimensional characteristics which prevent movement of the fecal matter across the surface. It is selected from a group consisting of a fibrous web, an open celled foam, a fibrous pile structure, entangled resilient fibers, silver knit, malivlieves, split corrugated web, tufted yarn, dimensioned needle-punch or mixtures thereof. The second superstructure is secured in the rear portion of the shell. In either case the superstructure is non-collapsible when wet, and, hence, maintains a void volume after being wetted, and after compression the superstructure restores void volume upon release of the compression.

The shell is formed from a moldable substance which is liquid-impermeable, is soft and flexible but when deformed by pressure returns substantially to its original configuration. For example, the shell may be a polyethylene-containing foam shell which is formed from a blown polyethylene-containing foam sheet which is subsequently subjected to molding by a thermal process. The shell generally has a boat-like shape and ranges in thickness from about 1/64" to about ¼" in thickness. The shell has a length which ranges from about 9" to about 22". The width in the front portion measured from one rim to another across the top space is from about 2" to about 7" and the width for the rear portion measured in the same manner is from about 3" to about 12" in the widest portion. The depth of the shell measured from a line extending across the width of the shell rim to the deepest portion across the width is at least 0.25" up to about 2". The first superstructure, which is placed in the front portion of the shell, in one embodiment is a carded nonwoven web formed from a resilient fiber such as polyester. The web is corrugated and stabilized to prevent the corrugations from separating or flattening when the web is wet and has pressure placed upon it.

The second superstructure placed in the rear portion of the shell is generally comprised of fibers which are substantially in the z direction as opposed to the xy plane. In one embodiment the corrugated web provided for the front portion is stabilized on both sides and is then slit horizontally through the web to provide a pile-like open web structure. This pile-like structure provides sufficient friction to retain the fecal waste matter so that it does not tend to migrate out the side of the product.

The absorbent medium placed in the front portion and optionally in the rear portion, is superabsorbent material, hydrophilic fibers, which are loosely compacted or formed into a nonwoven fiber, wadding, tissue, peat moss, mixtures thereof or the like.

In a specific embodiment of the present invention, a liquid-permeable fabric or woven covers the open side of the front portion of the product. This cover or facing is sealed to the rim of the shell thereby entrapping the first superstructure and the absorbent medium which have been placed in the front portion of the shell. It should be pointed out that the front portion and rear portion of the shell are separated by a liquid-impemeable barrier. If the urinary front portion does not have a facing or covering, the superstructure and, if necessary, the absorbent medium are affixed to the shell so as to remain in position even when wet. The second superstructure in the rear portion of the shell is preferably left open but is in any event secured in the shell so as to remain in position even when waste water is deposited thereon. Optionally, the second superstructure may have associated therewith an absorbent medium as described above.

The product of the present invention has a high impact capacity, i.e., the product accepts quickly and retains a relatively large quantity of liquid. Furthermore, the product does not leak or spill over. In other words, once liquid enters the product it remains entrapped within the product. The product also maintains its surface dry thereby keeping moisture away from the skin of the wearer. Still further, the product retains fecal waste matter thus keeping it from the clothing of the wearer. Also the product of the present invention permits air circulation in the region where the product is worn resulting in a high degree of comfort.

DETAILED DESCRIPTION OF INVENTION

Figure 1:
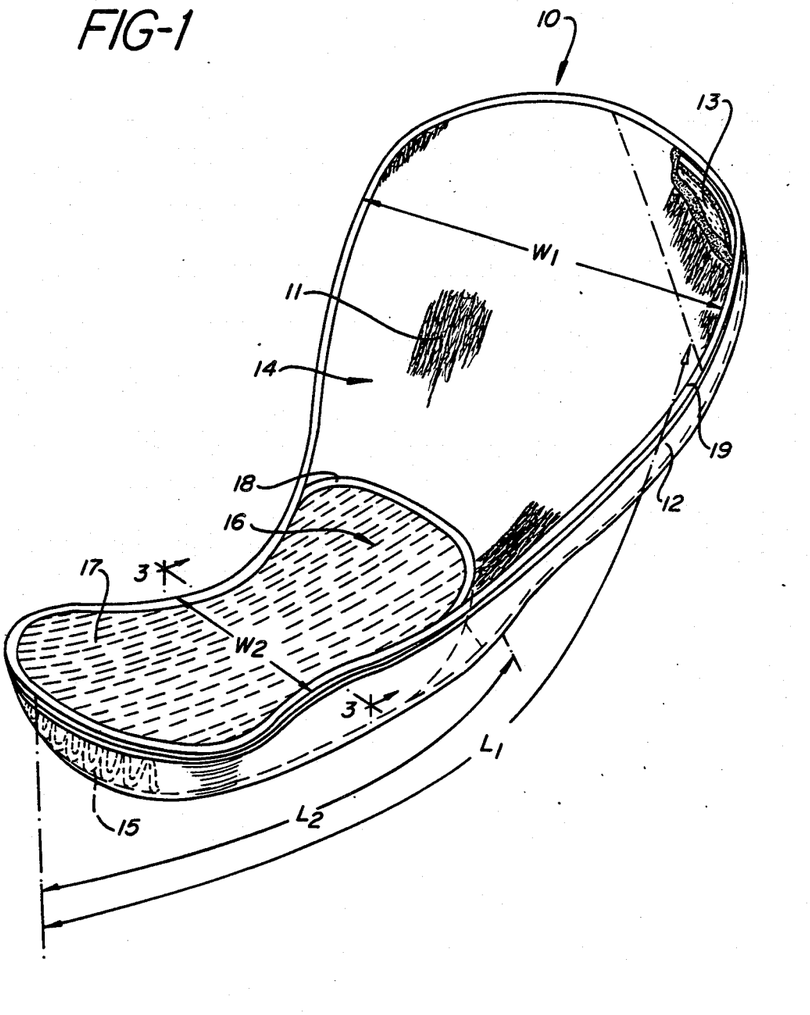
FIG. 1 is a perspective view of one embodiment of the present invention.

FIG. 1 is a perspective view of a disposable urinary and fecal waste containment product 10 which has a cross-linked ethylene polymer-containing foam shell 12 containing in the rear portion 14 a split portion of the corrugated web 11 and a superabsorbent containing fibrous web 13. The split corrugated web 11 and the superabsorbent containing web 13 are secured to the foam shell 12 in the rear portion 14 of the product. There is a segment of foam shell 18 which separates the front portion 16 from the rear portion 14. Contained in the front portion 16 of the shell is a corrugated web 15 which will be described in further detail later. The front portion 16 of the product 10 is covered by a liquid-permeable facing 17 which is adhered to the rim 18 of the shell 12, thus the urinary pad portion 16 is secured within the shell 12. At least the rear portion 14 of the shell has a lip 19 formed so that the side wall extends inwardly and then outwardly to form the lip 19. When the user applies pressure on the lip, the configuration of the side wall prevents the side from tilting outwardly thereby preventing any leakage.

The length of the product $L_1$ as shown in FIG. 1 ranges from about 9" to about 22". The length of the urinary portion $L_2$ of the product ranges from about 4" to about 12". The width of the rear portion 14 of the product is from about 3" to about 12", whereas the width of the front portion of the product identified as $W_2$ is from about 2" to about 7". The widths of the front and rear portions are somewhat proportional to the length, that is, if the length is approaching 22" of the overall product, then the widths will be approaching 12" and 7", whereas the length $L_2$ also increases as the overall length of the product increases.

Figure 1A:
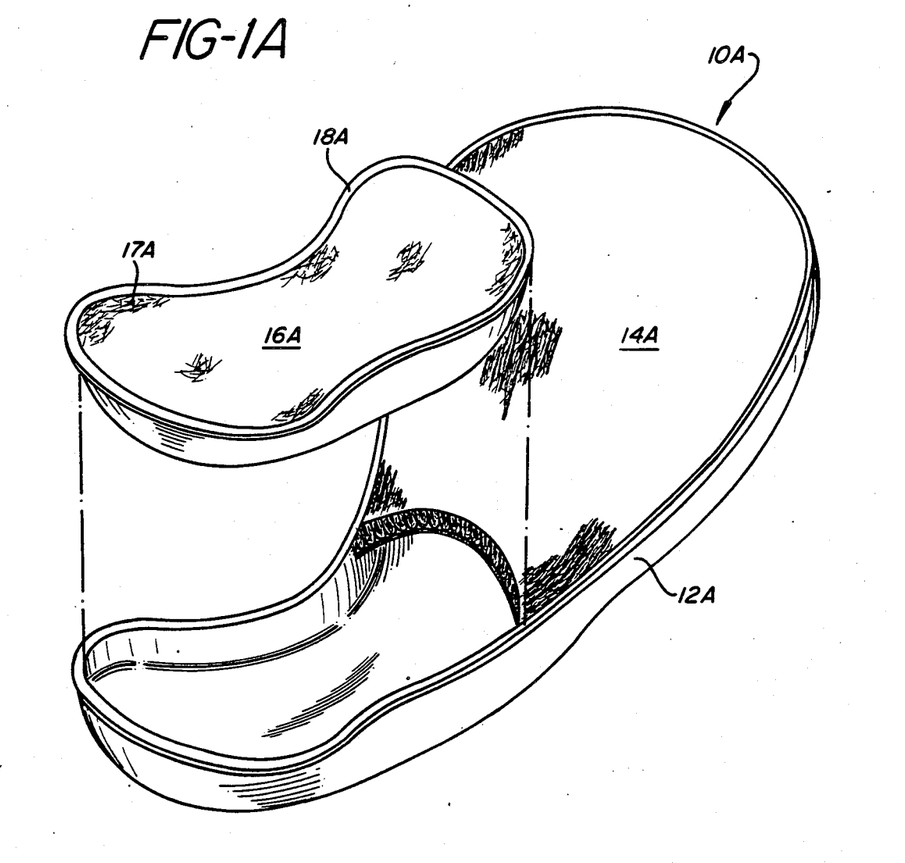
FIG. 1A is a perspective view of the parts of another embodiment of the present invention.

FIG. 1A depicts in a perspective view another embodiment of the product 10A which has a urinary pad portion 16A which is readily detachable from the shell 12A as shown in FIG. 1A. The shell portion 18A for the urinary pad is formed of the same foam as the shell 12A. This foam is a cross-linked ethylene polymer-containing liquid-impermeable foam. Generally the foam shell ranges from about 1/64" to about ¼" thick. The shell is preformed by a thermal molding process known in the art. The depth of the shell is at least about ¼" and preferably from ½ to 1". The depth of the shell for the urinary portion may be as deep as 2". The depth of the shell is measured by placing a line across from one rim to another and measuring the deepest point across that line.

Figure 2:
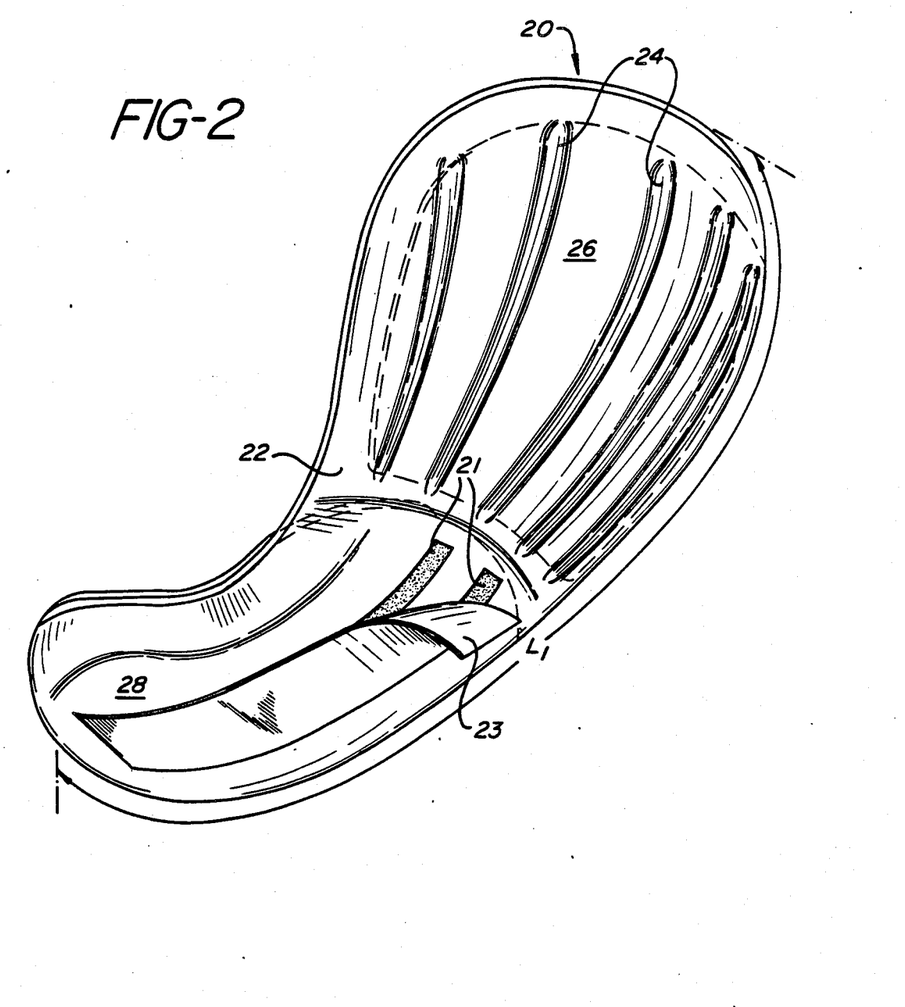
FIG. 2 is a perspective view of a different portion of one embodiment of the present invention.

FIG. 2 is a perspective view of the underside of the shell. Longitudinal indentations 24 placed in the rear portion of the shell assist in permitting the exterior of the shell to expand slightly when pressure is placed upon it by the wearer's sitting on the product. The front portion of the shell 28 in this embodiment is provided with adhesive strips 21 which are protected by a release strip 23 which is removed prior to application of the product to the underclothing of the wearer. The shell 20 is liquid-impermeable, flexible, preferably soft and is molded generally by a thermal molding process from substances such as polyethylene, polypropylene, polybutylene, ethylene vinyl acetate and other ethylene-containing polymers.

Figure 3:
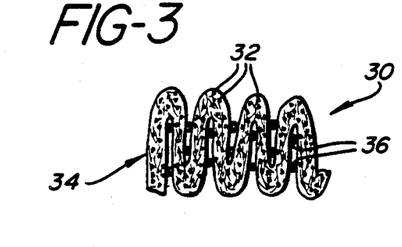
FIG. 3 is a cross-sectional view taken through lines 3—3 of FIG. 1.

FIG. 3 is a cross-sectional view of a portion of a typical corrugated web 30 used in the front portion or urinary pad portion of the product of the present invention. This portion 30 of the web shows the web 34 in a corrugated form wherein superabsorbent 32 has been placed among the fibers of the web. The web has been stabilized by thermal bonding of fusible fibers 36 which are in the blend of fibers forming the web 34.

Figure 4:
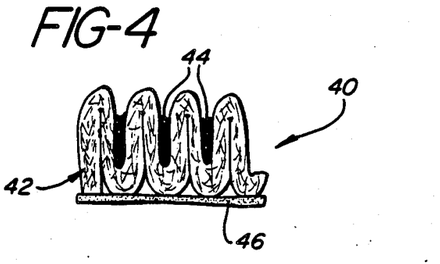
FIG. 4 is a cross-sectional view, like FIG. 3, of another embodiment of the present invention.

FIG. 4 depicts a cross-sectional view of another portion 40 of another corrugated web 42 suitable for use in the present invention. The corrugated web 42 is a fibrous web but does not contain any superabsorbent within the web fibers. Instead the superabsorbent 44 is placed between the corrugation folds of the web. Thus, as the web accepts and retains a void volume of liquid the liquid is readily in contact with the superabsorbent. The corrugated web 42 is stabilized by a thin coating of adhesive 46 placed on one side of the corrugated web 42. The corrugated web 42 would be placed in urinary pad which is the front portion of the present invention with the open corrugations toward the facing surface.

Figure 5:
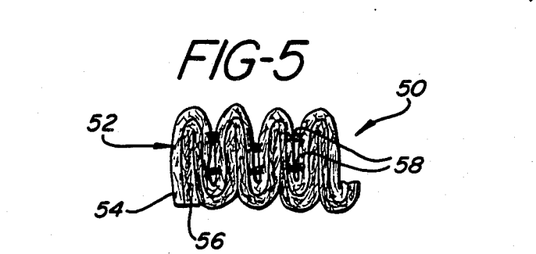
FIG. 5 is a cross-sectional view, like FIGS. 3 and 4, of still another embodiment of the invention.

FIG. 5 is a cross-sectional view in still another portion 50 of a corrugated web 52. This corrugated web 52 contains two layers 54 and 56. The layer 54 is a fibrous layer which has a lower capillary pressure than the second layer 56. A corrugated web 52 is stabilized by fusible fibers 58 which when the web is exposed to a temperature which substantially melts these fibers the corrugations in the web are fused together at least partially.

Figure 6:
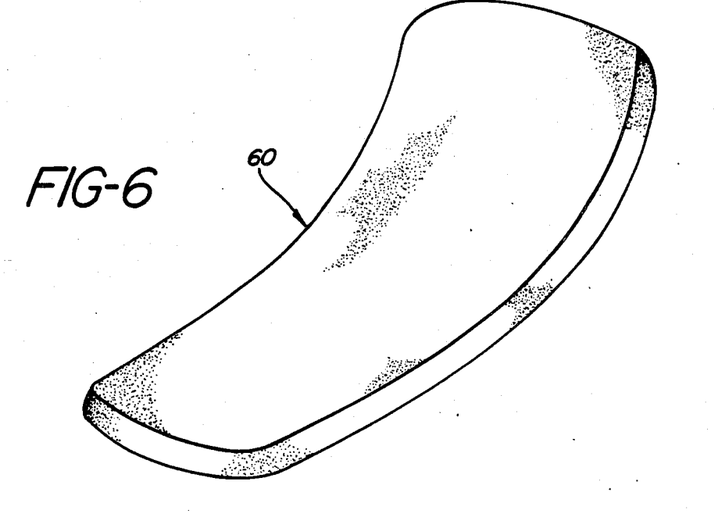
FIG. 6 is a perspective view of one element of a specific embodiment of the present invention.

FIG. 6 depicts an open cell foam 60 substantially rectangular in shape which can be placed in the front urinary pad section of the product of the present invention.

Figures 7, 8:
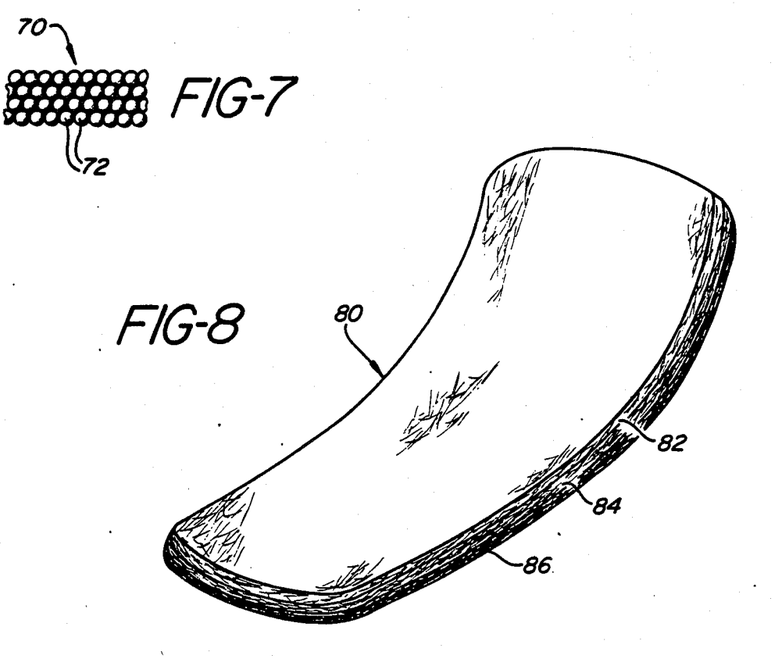
FIG. 7 is a cross-sectional view of a fragment of one element of a further embodiment of the present invention.
FIG. 8 is a perspective view of one element of a still further embodiment of the present invention.

FIG. 7 is a cross-sectional view of a fraction 70 of styrofoam beads 72 which forms the superstructure placed in the shell of the urinary pad portion of the present invention. These styrofoam beads 72 are placed in the shell so as to substantially fill the shell.

FIG. 8 is a perspective view of a multi-layer web structure 80 wherein the first layer 82 is of a lower density than is the second layer 84 and the second layer 84 is of a lower density than is the third layer 86. This multi-layered fibrous web would be placed in the shell of the urinary pad portion of the present product so that the first fibrous layer 82 is in contact with the facing.

Figure 9:
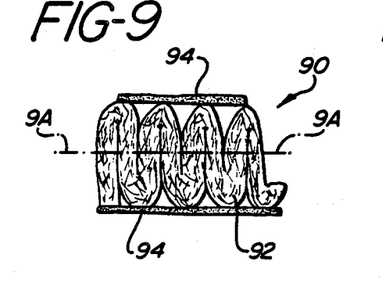
FIG. 9 is a cross-sectional view like FIGS. 3, 4 and 5 of another portion of one embodiment of the present invention.

The rear portion of the product of the present invention identified as portion 14 requires a different kind of superstructure from that used in the urinary pad portion. The superstructure of the fecal waste portion is at least slightly compressible and is capable of maintaining a small liquid void volume even when wet but it also requires that a pile-like formation of fibers is used so as to provide sufficient surface friction to retard migration of fecal matter across the pad surface. In accordance therewith, in FIG. 9, a cross-sectional view of a section of corrugated web 90 is depicted. The web 92 is generally a fibrous web such as a polyester web which has been corrugated and stabilized typically by use of adhesives 94 on both sides of the web. The web is then split along 9A—9A and the web appears as is depicted in FIG. 9A.

Figure 9A:
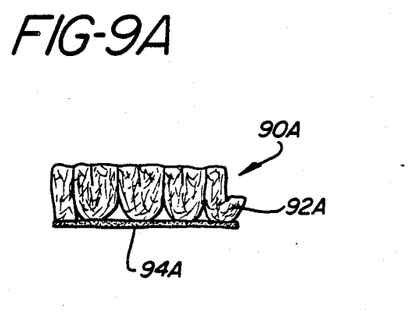
FIG. 9A is a cross-sectional view of the fragment of FIG. 9 as identified by lines 9A—9A.

In FIG. 9A a portion of corrugated web 90A is provided which has been stabilized by adhesive 94A. The portions of corrugated fibers 92A provide a tufted pile-like surface which is suitable to prevent migration of fecal matter when fecal matter is deposited thereon.

Figure 10:
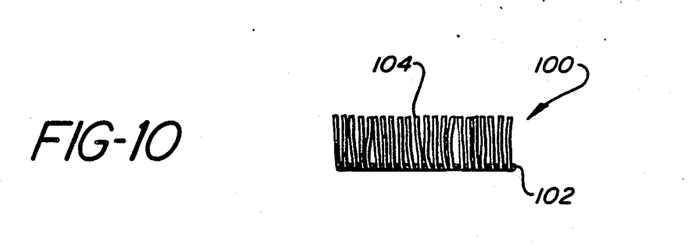
FIG. 10 is a cross-sectional view like FIG. 9 of a still further embodiment of the present invention.

Likewise in FIG. 10 a suitable needle-punch pole-like fabric is provided wherein the substrate 102 (either a scrim or batt of fibers) contains fibers 104 which have been secured in the substrate 102 by a needle-punch action. Thus, this fragment of product 100 is suitable for use in the rear portion of the product of the present invention.

The liquid-impermeable substantially flexible shell is formed from a moldable substance. The substance when molded should provide a liquid-impermeable, substantially flexible shell with a thickness ranging from about 1/64 inch to about ¼ inch. The shell when deformed should substantially return to its original shape. Substances which provide these characteristics and which are moldable by pressure, or thermal molding, or the like, are suitable. Particularly suitable for use in the present invention is a polyethylene-containing foam and/or an ethylene-containing polymer foam or mixtures thereof.

The expression "ethylene-containing polymer foam" used herein includes polyethylene homopolymer and ethylene-containing copolymers, preferably containing a major portion, by weight, of ethylene. It is preferred that the polymer present be crosslinked. Preferred co-monomers, for preparing the polymers, include vinyl acetate, acrylic and methacrylic acids and esters, such as ethyl acrylate. Blends of such polymers can also be used.

The foam shell is prepared by known thermal molding processing. The preferred formulation for forming the foam material is identified as Volara, Type A which is a crosslinked polyethylene foam. The product is manufactured and sold by Voltek, Inc., Lawrence, Mass. Preferably, the formulation is prepared in sheet form at approximately ⅛" in thickness. The sheet is subjected to thermal molding at a temperature of about 260° F. to form the foam shell. The shell is boat-like in shape, but is not limited thereto. The length of the shell ranges from about 9 inches to about 22 inches, with a width from about 2 inches to about 7 inches in the front portion and about 3 to about 12 in the rear portion. The thickness of the shell ranges from about 1/64" to about ¼". The depth of the shell is measured by extending a line horizontally from one rim to another in the center of the front or rear portion. The depth is then measured from that line to the base of the foam shell on the longitudinal axis. This depth ranges from about 0.25 to about 2.0". This foam shell may be made of other suitable compositions, which are soft and flexible and are liquid-impermeable.

The superstructure is non-collapsible when wet and consequently is able to maintain its void volume even after being wetted. The superstructure is comprised of hydrophobic, wet resilient, dry resilient fibers, fibrous web, foam or mixtures thereof. A fibrous web generally is formed from synthetic fibers such as polyethylene, polypropylene, polyester, polyamide fibers, bi-component fibers, copolymers thereof, mixtures thereof and the like. However, hydrophobic cellulosic fibers such as hydrophobic rayon may also be used. The fibers are placed in the web by known means such as by carding to form a web which is then stabilized if needed. Stabilization may be achieved by heat-through bonding, adhesive bonding, point embossing with heat or adhesive (or both), needle punching, use of water jets and the like. The stabilizing process is selected according to the fibers used and the process used to form the web. Other suitable procedures for forming a web include air-laying, wet-laying, spun bonding, laying of melt-blown fibers, spread tow, and other known techniques. A typically suitable web has a dry bulk of at least about 10 cc/gm and a weight less than about 4 oz/yd$^2$.

In a preferred embodiment, a fibrous web is corrugated and stabilized so as to prevent loss of corrugation when the fibrous web becomes wet. Corrugating or transverse folding of the web may be carried out by procedures such as that in U.S. Pat. No. 4,111,733. Generally, the web corrugations will range from about 3 to 6 or even 8 per inch of corrugated web, and the web thickness will be from about ¼ to about 3", preferably from about ½ to about 1½" thick. One method of stabilizing the corrugations in the web is accomplished by using an adhesive which may be a latex binder or other known adhesive. The corrugated web is sprayed with the adhesive on one corrugated surface thereof, or if desired on both corrugated surfaces. The adhesive is cured and the web thus stabilized. Another method of stabilizing the web is by adding a small portion of fusible fibers to the web fibers before or after the web is made. These fusible fibers have a lower melting point than the remaining fibers and when the corrugated web is subjected to temperatures sufficient to melt the fusible fibers, light bonding is provided between the corrugations.

In one specific embodiment, a blend of staple polyester fibers with a minor portion of fusible fibers such as lower melt polyester fibers are carded to form a web. The web is subsequently lightly bonded by passing hot air through the fibers making the fusible fibers tacky so as to stick to each other and the staple fibers to provide the desired degree of integrity to the corrugated web structure.

Fibrous webs may be used in the urinary portion in non-corrugated form as well. For instance, a high loft, low density, stable fibrous web may be placed in the shell and either adhered to the shell wall or provided with a facing covering the web to provide a satisfactory urinary pad. If the desired thickness is not available in the web, more than one layer of the web may be used but preferably the capillary pressure provided by each web layer increases as the layers are placed away from the facing. In an example with three layers of fibrous webs, the top layer, that is the layer closest to the open side of the shell, has the lowest capillary pressure, the mid layer has a high capillary pressure than the first layer but a lower capillary pressure than the third and last layer. Hence, the liquid leaves the surface rapidly or it is drawn into the lower layers.

What appears to be only a small difference in capillary pressure is all that is required for one layer to attract and drain liquid from an adjacent layer. The force causing a liquid to enter a cylindrical capillary is expressed by the equation:

$$P = (2v \cos \theta)/r$$

wherein the force is represented by the capillary pressure and

P is the capillary pressure,
$v$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and also increases with narrower capillary radii so that narrower capillaries will draw liquid from wider ones.

The relative wickability between a first fibrous layer and a second layer is affected by both the relative densities of the layers and the relative wettability of the individual fibers in each layer. The individual fibers of the second layer preferably have substantially smaller liquid fiber contact angles than those of the first fibrous layer overcoming the density difference and providing a significant overall increase in capillary pressure to absorb liquid into the second layer.

The fibers of the second layer of fibers and any subsequent layer of fibers (or particles) and/or the density of the layer are selected to create a significant difference in capillary pressure from the first fibrous layer.

The second fibrous (or particle) layer is generally comprised of fibers having a lower liquid-contact angle or wherein the layer is provided with a narrower capillary radii. Examples of such fibers include hydrophilic fibers such as rayon fibers, cellulosic fibers, or peat moss, or mixtures thereof, or acrylic fibers, or the like. Cellulosic fibers include wood pulp fibers, cotton linters and the like. This second layer of hydrophobic fibers provides a suitable absorbent medium.

The wood pulp fibers generally are those that are used to form the fluff or fibrous batt layer in conventional absorbent products such as disposable diapers, sanitary napkins, etc. Other cellulosic fibers that might be used are rayon fibers, flax, hemp, jute, ramie, cotton, and the like. The fiber, or peat moss, or mixtures thereof are placed in such a way as to form a layer in which the particles are close to one another so as to promote wicking of liquid in the plane of the layer.

The second layer can be performed and placed next to the first fibrous layer or, the particles (fibers or peat moss or mixtures thereof) can be air-laid or wet-laid, or otherwise combined with the first fibrous layer before any transverse folding or corrugating takes place.

The multiple layer structure may be corrugated or simply used in its multiple layer form in the urinary portion.

Another material suitable for making the superstructure of the urinary portion is a foam. The foam should be slightly compressible, reasonably flexible, and must be able to maintain a void volume, i.e., hold liquid reasonably when wet. The foam needs to be in a form that allows liquid to enter the entire foam structure and at the same time has at least some collapse resistance sufficient to maintain the void volume of the foam. A foam-type structure which in its unaltered form that is not satisfactory is a sponge. Although a sponge does have the collapse resistance and has the necessary void volume, a sponge tends not to provide adequate impact capacity. In other words, the liquid upon initial contact is not immediately entrapped in the void volume space. However, if a sponge is chopped up into pieces or if holes are put into the sponge, so as to permit the liquid to enter a void space initially, the sponge will perform satisfactorily.

The foam may be placed in the front portion of the shell in sheet form whereupon if the sheet is sufficiently preferable that there by a capillary difference between the layers as discussed hereinbefore. The foam may be placed in the shell in chopped pieces or perhaps in the form of beads such as styrofoam beads. The foam may be thick and cast into the shell so as to form fit the shell. Suitable foams include polyurethane foams, polystyrene foams, and the like.

The superstructure for the urinary portion is selected so as to provide sufficient void volume to hold a normal liquid void and impact capacity to receive the liquid rapidly enough to prevent a run off. Also, the superstructure should retain the liquid even under normal pressure such as that provided by the wearer of the pad when sitting down or moving the legs thereby compressing the urinary pad.

The first superstructure, i.e., the one provided for in the urinary pad portion, has been described in detail. Most of these superstructures will work as the second superstructure, i.e., the one for the fecal waste containment portion of the product. However, it has been found that a superstructure which is fibrous having a pile-like structure is particularly desirable. A pile-like fibrous structure is obtained by providing a corrugated fibrous web stabilizing the web on both exterior sides of the web and then slitting the web as shown in FIG. 9A through the central portion of the corrugated web to provide a pile-like fibrous structure. Other suitable fibrous structures include needle-punch structures, silver knit, malivlieves, tufted yarn, structure dimensioned needle-punch and the like. If it appeared desirable a facing could be placed over the superstructure of the fecal waste containment. However, generally it is preferred to retain the surface area of the pile-like superstructure for provision of the friction sufficient to prevent migration of the fecal waste matter. If a facing or covering is provided over the superstructure in the rear portion of the present product, the facing will be adhered to the rim of the shell so that the superstructure remains in place. If a facing or covering is not used then the superstructure should be secured in the shell so that even when wet the superstructure remains in place in the shell. Securement can be achieved by thermal bonding, application of adhesive, and the like.

The superstructure provided for the rear portion of the product need not provide the high liquid retention characteristics of the urinary portion of the product. However, it is desirable in the rear portion of the product to provide some liquid retention characteristics so that any liquid waste associated with the fecal waste is readily received and retained in the product. In conjunction therewith, wood pulp fibers and other cellulosic materials such as those discussed in the urinary pad portion are suitable to use. A foam portion or a sponge-like portion placed beneath the superstructure would assist in liquid retention. Any suitable means of retaining liquid at the base of the superstructure is satisfactory for use in the fecal waste containment portion of the present product.

One means of providing an increase in the liquid capacity of the product whether it be the urinary portion or the fecal waste containment portion is the placement of superabsorbent in intimate contact with at least a portion of the superstructure.

The superabsorbent, present either on the fibers of a web or placed in the folds of a corrugated web, or otherwise associated with the void volume portion of the superstructure, is generally a water-insoluble, water-swellable polymeric substance capable of absorbing water in an amount which is at least 10 times the weight of the substance in its dry form. The superabsorbent is in the form of fibers, spheres, particles, bits of film, globules, webs, film or the like, or may be applied in the form of a liquid monomer solution which is subsequently polymerized. The superabsorbent prepared by polymerization of a monomer solution placed on fibers in a web is most frequently in the form of globules and bits of film-like particles in the web structure.

One type of superabsorbent material provides particles or fibers which may be described chemically as having a backbone of natural or synthetic polymers with hydrophilic groups or polymers containing hydrophilic groups being chemically bonded to the backbone or an intimate mixture therewith. Included in this class of materials are such modified natural and regenerated polymers as polysaccharides, including for example, cellulose and starch and regenerated cellulose which are modified by being carboxyalkylated, phosphonoalkylated, sulfoalkylated, or phosphorylated to render them highly hydrophilic. Such modified polymers may also be cross-linked to improve their water-insolubility.

These same polysaccharides may also serve, for example, as the backbone on to which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula:

wherein A and B are selected from the group consisting of $-OR^3$, $-O$(alkali metal), $-OHNH_3$, $-NH_2$, wherein $R^1$, $R^2$, and $R^3$ are selected from the group consisting of hydrogen and alkylene having 1 to 4 or more carbon atoms wherein r is an integer having a value of 0 to about 5000 or more, s is an integer having a value of 0 to about 5000 or more, r plus s is at least 500, p is an integer having a value of 0 or 1, and q is an integer having a value of 1 to 4. The preferred hydrophilic chains are hydrolyzed polyacrylonitrile chains and copolymers of polyacrylamide and polysodium acrylate.

In addition to the modified natural and regenerated polymers, the hydrocolloid component may comprise wholly synthetic hydrophilic particles. Examples of those now known in the art are polyacrylonitrile fibers which may be modified by grafting moieties thereon such as polyvinylalcohol chains, polyvinyl alcohol itself, hydrophilic polyurethane, poly(alkyl phosphonates), partially hydrolyzed polyacrylamides (e.g., poly(N-N-dimethylacrylamide), sulfonated polystyrene, or a class of poly(alkyleneoxide). These highly hydrophilic synthetic polymers may be modified by other chemical treatments such as cross-linking or hydrolysis. Further examples known in the art are the non-ionic polymers such as polyoxyethylene, polyoxypropylene, and mixtures thereof which have been suitably cross-linked, either chemically or by irradiation. Still another more recent type is a derivative of isobutylene-maleic anhydride copolymer. Hydrophilic polymers formed from water-soluble acrylate monomers, such as sodium, potassium, ammonium, (or a combination of cations), acrylate, may be placed on a fibrous web by spraying or otherwise placing a solution thereon, followed by polymerization and cross-linking, for example, by irradiation.

In addition, naturally occurring materials such as gums may be used. Examples of such suitable gums include guar gums, acacia gums, locust bean gums and the like.

The superabsorbent may be placed in the bottom of the shell prior to the placing of the superstructure in the shell or it may be a part of the superstructure. If the superstructure is a fibrous web having substantially uniform density throughout, the superabsorbent is best placed between the fibrous web and the inside surface of the shell. Another alternative method of placing superabsorbent on or within a fibrous web, is by spraying a monomer solution on the fibrous web or perhaps even saturating the web with a monomer soluble followed by polymerization and cross-linking of the monomer. One typical way to polymerize the monomer is by use of irradiation. This places the superabsorbent substantially evenly throughout the fibrous web and affixes the superabsorbent in such a manner that the superabsorbent globules or particles are within a void volume sufficient to permit them to swell substantially to completion.

If the web is corrugated or transversely folded, superabsorbent can be placed within the folds provided it is sufficiently associated with the void volume that the swelling of the superabsorbent can occur. If the web is a multiple layer web, it is desirable to associate the superabsorbent with the web having the highest capillary pressure. Another concept is the placement of superabsorbent in a pre-established situation, such as within a moisture-permeable bag to form a packet, or a pocket, or the like. If the superabsorbent is in the form of granules, it may be desirable to moisten the granules and then fix them in place either on the web or in the foam or at the surface of the shell, which will be in contact with the superstructure.

In summation, the superstructure can be any structure which allows liquid to enter the structure rapidly, that retains the liquid, and provides collapse resistance so that the liquid is not pressed out of the superstructure, until the liquid is absorbed by the absorbent medium whereupon the void volume of the superstructure is again available for more liquid.

The product of the present invention does not require a facing or cover on either portion, but if no facing or covering is used, then it is necessary to secure the superstructure within the shell so that prior to or during use the superstructure does not separate itself from the shell. If, however, it is desirable to use a covering of facing, the covering or facing placed over the open side of the shell is liquid-impermeable and is readily sealable to the outer rim of the shell so as to entrap the superstructure in the shell. Suitable coverings or facings for the urinary portion include fabrics, nonwoven webs, perforated films, and the like. Preferably, the facing is a thermoplastic substance which can be heat sealed to the rim of the liquid-impermeable shell.

The product of the present invention is worn by the wearer in the crotch region, and for simplicity is secured to the underclothing of the wearer. Securement may be effected by adhesive lines or strips on the exterior of the shell or may simply secure itself to the underclothing by means of friction. If the product is to be secured by friction, a material for manufacturing the shell is selected which will provide sufficient friction or a material is coated on the exterior of the shell to provide such friction.

Examples for the preparation of the present invention are as follows. These examples are not intended to be limiting in any way and extensions and modifications thereof, without departures from the spirit and scope of the invention, will become apparent from these examples.

EXAMPLE I

A flexible shell for the urinary portion is formed by thermoforming an ethylenevinyl acetate copolymer blend foam sheet. The urinary portion shell has a length of 8 inches, a width at the widest point of 4⅜ inches, and a width at the central portion at its narrowest point of 3¾ inches. The shell is ⅞ inches deep at the center from a line extending across the center from the edge of each rim of the shell.

The superstructure placed in the shell consists of a two-layer fibrous web which has been corrugated. The first fibrous layer comprises 50% by weight of the final corrugated web. It consists of 75 parts of polyester fibers with 25 parts of polyester binder fibers. The polyester binder fibers have a lower melting point than the remaining polyester fibers. The average denier of the fibers is about 15. The web is formed by a conventional carding process providing a web having a weight of about 2 oz. per sq. yd. The second layer is carded directly onto the first layer and is formed from acrylic fibers having a denier of about 1.5 which are a blend of 40 parts of the acrylic fibers with 10 parts of the same binder fibers used in the first layer. The two layer web structure is corrugated and heat set at about 315° F. The corrugated two layer web is ¾" high and has approximately 4.5 folds per inch of corrugation. A corrugated web has a weight of about 12 oz. per sq. yd.

The absorbent medium provided for in this urinary portion of the present product is a blend to superabsorbent identified as 10SH manufactured and sold by Mitsubishi Company, Tokyo, Japan and mineral oil. Four parts of superabsorbent are admixed with one part of mineral oil. This blend is placed on the bottom fiber layer of the two layer web and between the folds to a depth of approximately ¼ to ½". The amount of the blend added is approximately 1 gram of the superabsorbent mineral oil blend per gram per superstructure.

A nonwoven fabric made from bicomponent fibers of polyester core and polyethylene sheath having a weight of about 0.5 oz. per sq. yd. is heat sealed to the rim of the shell of the urinary cushion of the product to provide a facing or covering for the front portion.

The superstructure provided for the fecal waste containment rear portion of the product is made by blending 40% by weight of polyester fibers with 40% by weight of acrylic fibers and 20% by weight of binder fibers and a web is formed by carding. The web has a basis weight of about 2 oz. per sq. yd. This web is corrugated to a height of about 1.5" having about six corrugations per inch. The corrugated web has a basis weight of 30 oz. per sq. yd. The acrylic fibers placed in the web provide the necessary absorbent medium in intimate contact with the superstructure of the fecal waste containment portion. The web is stabilized by application of a latex type adhesive identified as Rhoplex NW1715 manufactured and sold by Rohm and Haas Corp., in an amount of about 2 gm per sq. yd. so as to stabilize the corrugated web against collapse or separation when wet. The web is stabilized on both sides and subsequently is slit horizontally to provide two sections of web each of which is approximately the same thickness, i.e., a thickness of about ¾".

Additional adhesive is applied on the adhesive stabilized side of the corrugated web and the web is placed in and secured in the rear portion by the adhesive sticking to the shell. The urinary portion of the product is tested by adding 20 cc per second assimulated urine liquid. After the addition of the liquid, the product is left in its receiving position, i.e., substantially horizontally for 5 seconds and then is turned so that the corrugations, if the superstructure is a corrugated product, are vertical. With a discharge of 100 cc the retention of the product exhibited is 98%. A discharge of 150 cc exhibited a retention of 85% and a discharge of 200 cc provides a retention of about 82%.

The fecal portion of the produce proves satisfactory in that deposit of fecal waste matter exhibits immediate acceptance and retention of any liquid portion and retains the fecal matter substantially in the place of discharge without migration to another portion of the product or outside the product.

It becomes readily apparent from the above example that the present invention provides a highly satisfactory product for use by incontinent adults who are active people. It is truly surprising that a structure can be provided which will hold at least 80% of a 200 cc discharge of urine after merely 5 seconds contact time and simultaneously retain normal discharge of fecal matter witout soiling of surrounding clothing.

From the foregoing, it will be observed that numerous variations and modifications may be effected without departing from the true spirit and scope of the novel concept of this invention.

We claim:

1. A disposable urinary and fecal waste containment product comprising a liquid-impermeable substantially flexible shell having a depth of at least about 0.25 inch; having a front urinary portion and a rear fecal portion; said front portion being narrower and having an area less than 70% of the area of said rear portion, said front urinary portion having a first superstructure placed in and substantially filling said front portion of said shell and an absorbent medium in contact with at least a portion of said superstructure; said superstructure being a corrugated fibrous web comprising hydrophobic wet resilient, dry resilient fibers, which is non-collapsible when wet and capable of maintaining a void volume when wetted; and said rear portion having a second superstructure placed in and substantially filling said rear portion of said shell said superstructure being non-collapsible when wet and capable of maintaining a void volume when wetted said second superstructure being comprised of a fibrous web, open cell foam, a fibrous pile structure, sliver knit, malivlieves, split corrugated web tufted yarn, dimensioned needle punch or mixtures thereof; said second superstructure being secured in said rear portion of said shell.

2. The disposable product of claim 1 having a liquid barrier between said rear portion and said front portion.

3. The disposable product of claim 1 wherein said superstructure of said rear portion is comprised of a split corrugated web comprised substantially of polyester fibers.

4. The disposable product of claim 1 wherein said absorbent medium is comprised of hydrophilic fibers, nonwoven web of hydrophilic fibers, wadding, tissue, peat moss, superabsorbent material, or mixtures thereof.

5. The disposable product of claim 1 wherein said shell is an ethylene-containing polymer foam shell having a thickness of about 1/64 inch to about ¼ inch.

6. The disposable product of claim 5 wherein said shell is a thermal formable substance.

7. The disposable product of claim 1 wherein said corrugated fibrous web is comprised of polyester fibers.

8. The disposable product of claim 1 wherein said absorbent medium is comprised of superabsorbent material.

9. The disposable product of claim 1 wherein said absorbent medium is comprised of loosely compacted wood pulp fibers.

10. A disposable urinary and fecal waste containment product comprising a liquid-impermeable substantially flexible shell having a depth of at least about 0.25 inch; having a front urinary portion and a rear fecal portion; said front portion being narrower and having an area less than 70% of the area of said rear portion, said front urinary portion having a first superstructure comprising polyester fibers, placed in and substantially filling said front portion of said shell, and an absorbent medium comprising acrylic fibers and superabsorbent material, in contact with at leaast a portion of said superstructure; said polyester fibers and said acrylic fibers forming a two layered web which is a corrugated web; said superstructure being non-collapsible when wet and capable of maintaining a void volume when wetted; and said rear portion having a second superstructure placed in and substantially filling said rear portion of said shell said superstructure being non-collapsible when wet and capable of maintaining a void volume when wetted said second superstructure being comprised of a fibrous web, open cell foam, a fibrous pile structure, sliver knit, malivlieves, split corrugated web, tufted yarn, dimensioned needle punch or mixtures thereof; said second superstructure being secured in said rear portion of said shell.

11. The disposable product of claim 8 wherein said superabsorbent material is comprised of polysodium acrylate.

12. The disposable product of claim 1 wherein said shell is a cross-linked polyethylene foam shell having a thickness from about 1/64 inch to about ¼ inch.

13. The disposable product of claim 1 wherein said shell in said front portion has a depth from about 0.5 to about 2.5 inches.

14. The disposable product of claim 13 wherein said shell in said front portion has a depth from about 0.5 to about 1.5 inches.

15. A disposable urinary and fecal waste containment product comprising a crosslinked ethylene-containing polymer foam liquid-impermeable substantially flexible shell having a depth of at least about 0.25 inch; having a front urinary portion and a rear fecal portion; said front portion being narrower and having an area less than 70% of the area of said rear portion, said front urinary portion having a first superstructure placed in and substantially filling said front portion of said shell and an absorbent medium in contact with at least a portion of said superstructure said absorbent medium comprising a corrugated layer of acrylic fibers and superabsorbent material; said superstructure being non-collapsible when wet and capable of maintaining a void volume when wetted; and said rear portion having a second superstructure placed in and substantially filling said rear portion of said shell said second superstructure being non-collapsible when wet and capable of maintaining a void volume when wetted, said second superstructure being comprised of a fibrous web, open cell foam, a fibrous pile structure, sliver knit, malivlieves, split corrugated web, tufted yarn, dimensioned needle punch or mixtures thereof; said second supersturcture being secured in said rear portion of said shell.

16. The disposable diaper of claim 15 having a liquid barrier between said rear portion and said front portion.

17. The disposable product of claim 15 wherein said supersturcture of said rear portion is comprised of a split corrugated web comprised substantially of polyester fibers.

18. The disposable product of claim 15 wherein said absorbent medium is comprised of hydrophilic fibers, nonwoven web of hydrophilic fibers, wadding, tissue, peat moss, superabsorbent material, or mixtures thereof.

19. The disposable product of claim 15 wherein said first superstructure is comprised of hydrophobic, wet resilient, dry resilient, fibers, fibrous web, foam or mixtures thereof.

* * * * *